US00PP25533P3

(12) United States Plant Patent
Larse

(10) Patent No.: US PP25,533 P3
(45) Date of Patent: May 12, 2015

(54) STRAWBERRY PLANT NAMED 'DANI'

(50) Latin Name: *Fragaria×ananassa*
Varietal Denomination: DANI

(71) Applicant: Sweet Darling Sales, Inc., Aptos, CA (US)

(72) Inventor: John Larse, Aptos, CA (US)

(73) Assignee: Sweet Darling Sales Inc., Aptos, CA (US)

( * ) Notice: Subject to any disclaimer, the term of this patent is extended or adjusted under 35 U.S.C. 154(b) by 140 days.

(21) Appl. No.: 13/986,675

(22) Filed: May 23, 2013

(65) Prior Publication Data

US 2013/0340135 P1 Dec. 19, 2013

Related U.S. Application Data

(60) Provisional application No. 61/650,798, filed on May 23, 2012.

(51) Int. Cl.
*A01H 5/00* (2006.01)

(52) U.S. Cl.
USPC ..... Plt./209

(58) Field of Classification Search
USPC ..... Plt./209
See application file for complete search history.

*Primary Examiner* — Annette Para
(74) *Attorney, Agent, or Firm* — Cooley LLP

(57) ABSTRACT

The present invention provides a new and distinct strawberry variety designated as 'DANI' (a.k.a., '105429').

4 Drawing Sheets

Latin name of genus and species: *Fragaria×ananassa.*
Varietal denomination: 'DANI'.

BACKGROUND OF THE INVENTION

The present invention relates to a new and distinct early day-neutral strawberry variety designated as 'DANI' (a.k.a. '105429'). This new variety is the result of a controlled-cross between a female parent cultivar designated '2002' and a male parent cultivar designated '1706' (both unpatented, proprietary cultivars) made by the inventor and first fruited in Watsonville, Calif. growing fields.

Following selection and during testing, the plant was originally designated '105429' and subsequently named 'DANI'. The new variety of 'DANI' was asexually reproduced via runners (stolons) by the inventor at Watsonville, Calif. Asexual propagules from the original source have been tested in the Watsonville growing fields and, to a limited extent, growing fields in low and high elevation. The properties of this variety were found to be transmissible by such asexual reproduction. The cultivar is stable and reproduces true to type in successive generations of asexual reproduction.

SUMMARY OF THE INVENTION

This invention relates to a new and distinctive early producing day-neutral type cultivar designated as 'DANI'. It is primarily adapted to the climate and growing conditions of the central coast of California. This region provides the necessary temperatures required for it to produce a strong vigorous plant and to remain in fruit production from April through October. The nearby Pacific Ocean provides the needed humidity and moderate day temperatures and evening chilling to maintain fruit quality for the production months.

The following traits in combination distinguish strawberry variety 'DANI' from the known strawberry varieties. Plants for the botanical measurements in the present application were grown as annuals. In the following description, color references are made to The Royal Horticultural Society Colour Chart, 1995 Edition, except where general terms of ordinary dictionary significance are used.

The following are the most outstanding and distinguishing characteristics of this new variety when grown under normal conditions in Watsonville, Calif.

High early yield; and

Weather resistant.

When 'DANI' is compared to the proprietary female parent '2002', it produces earlier fruit albeit in smaller quantities and size.

When 'DANI' is compared to the proprietary male parent '1706', it is very similar in features but its denser leaves provide the fruit with more weather resistance.

When 'DANI' is compared to 'Albion' (U.S. Plant Pat. No. 16,228), 'DANI' produces fruit earlier. Although it is not a significant earlier harvest, the load is heaviest at the beginning of its harvest interval than 'Albion's. 'DANI' fares better during variable wet weather as well as during transportation.

DESCRIPTION OF THE DRAWINGS

The accompanying color photographs depict various characteristics of the 'DANI' cultivar at various stages of development as nearly true as possible to make color reproductions.

DETAILED BOTANICAL DESCRIPTION

Figure 1:
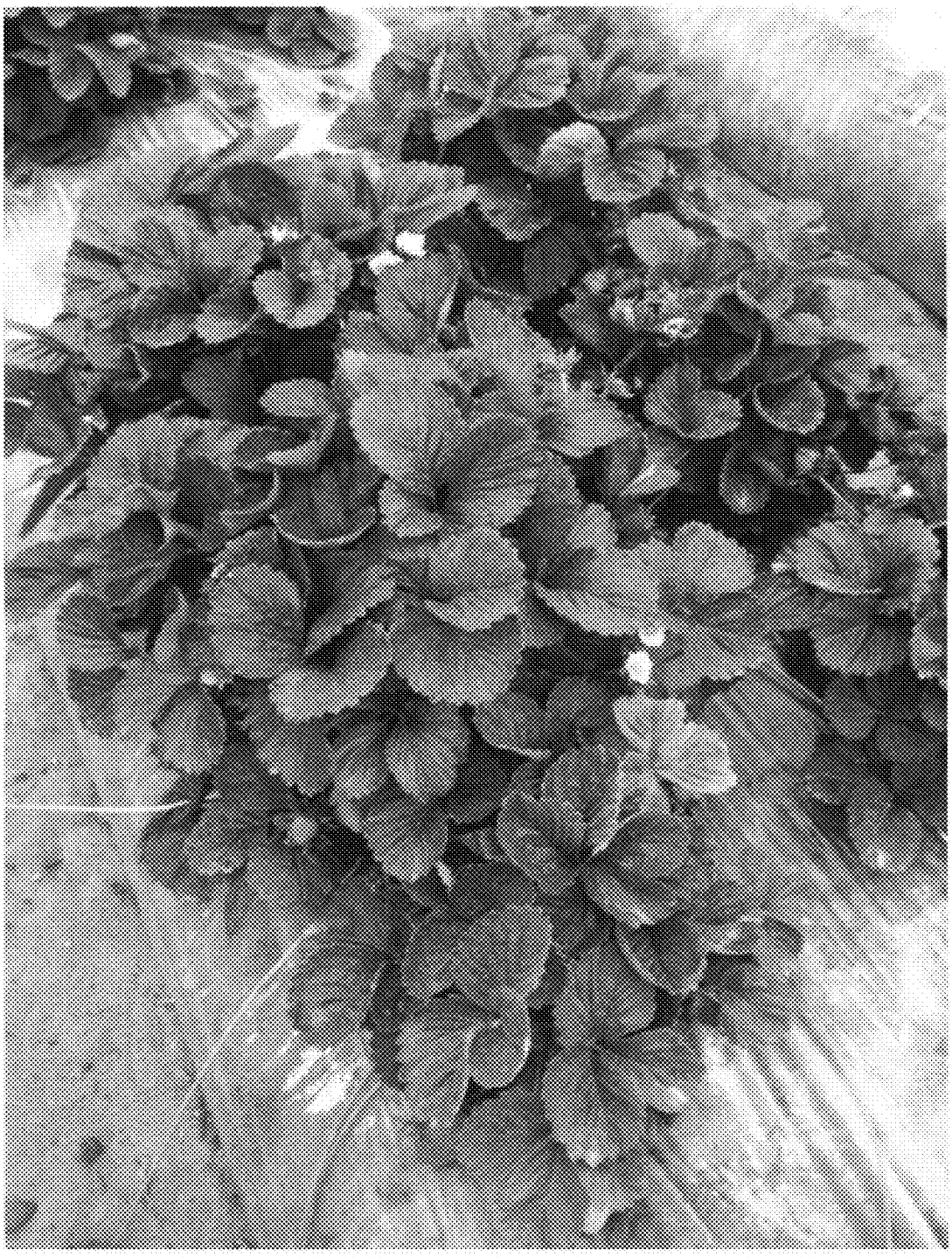
FIG. 1 shows 'DANI' plant in early May.
Figure 2:
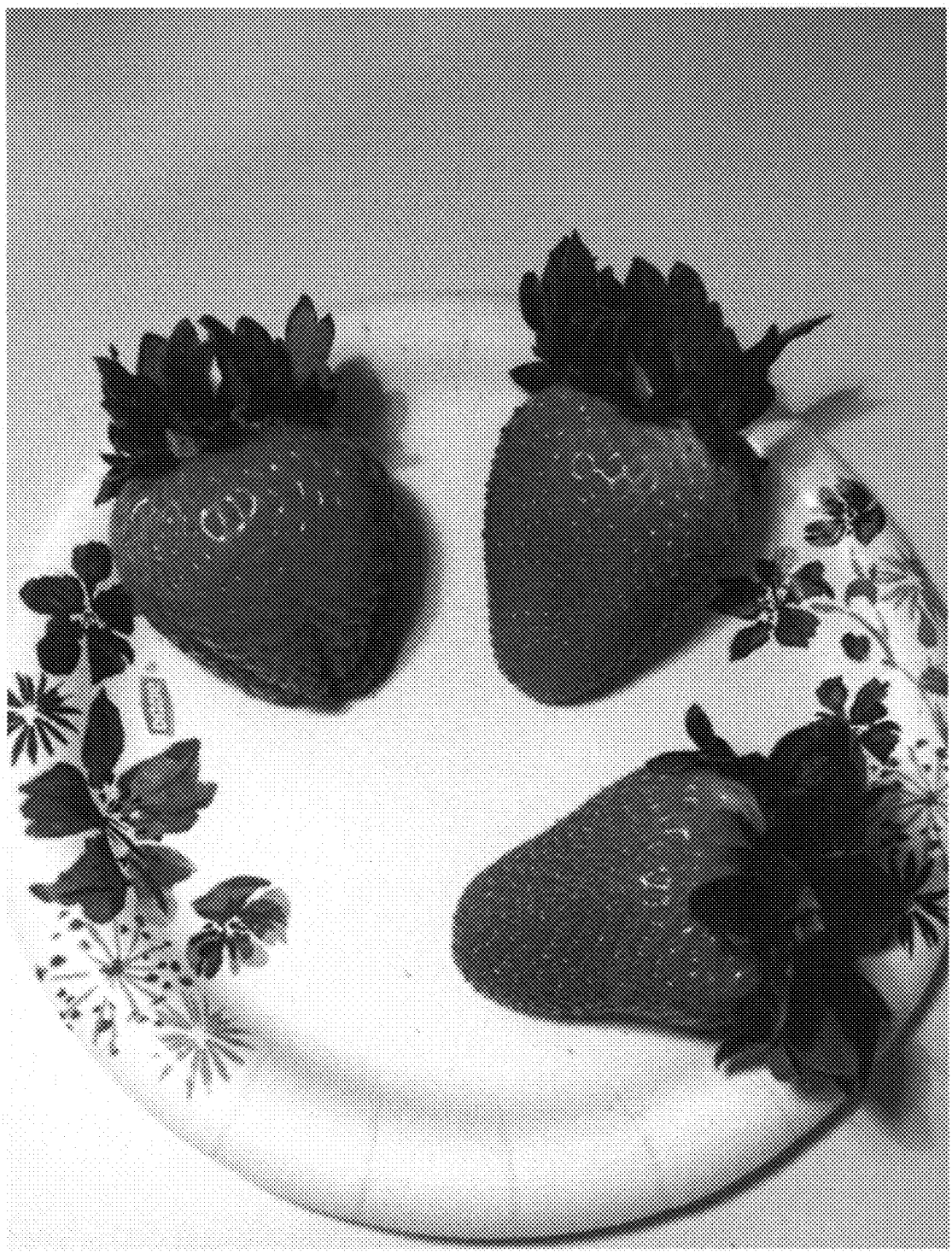
FIG. 2 shows 'DANI' strawberries from early May picking.
Figure 3:
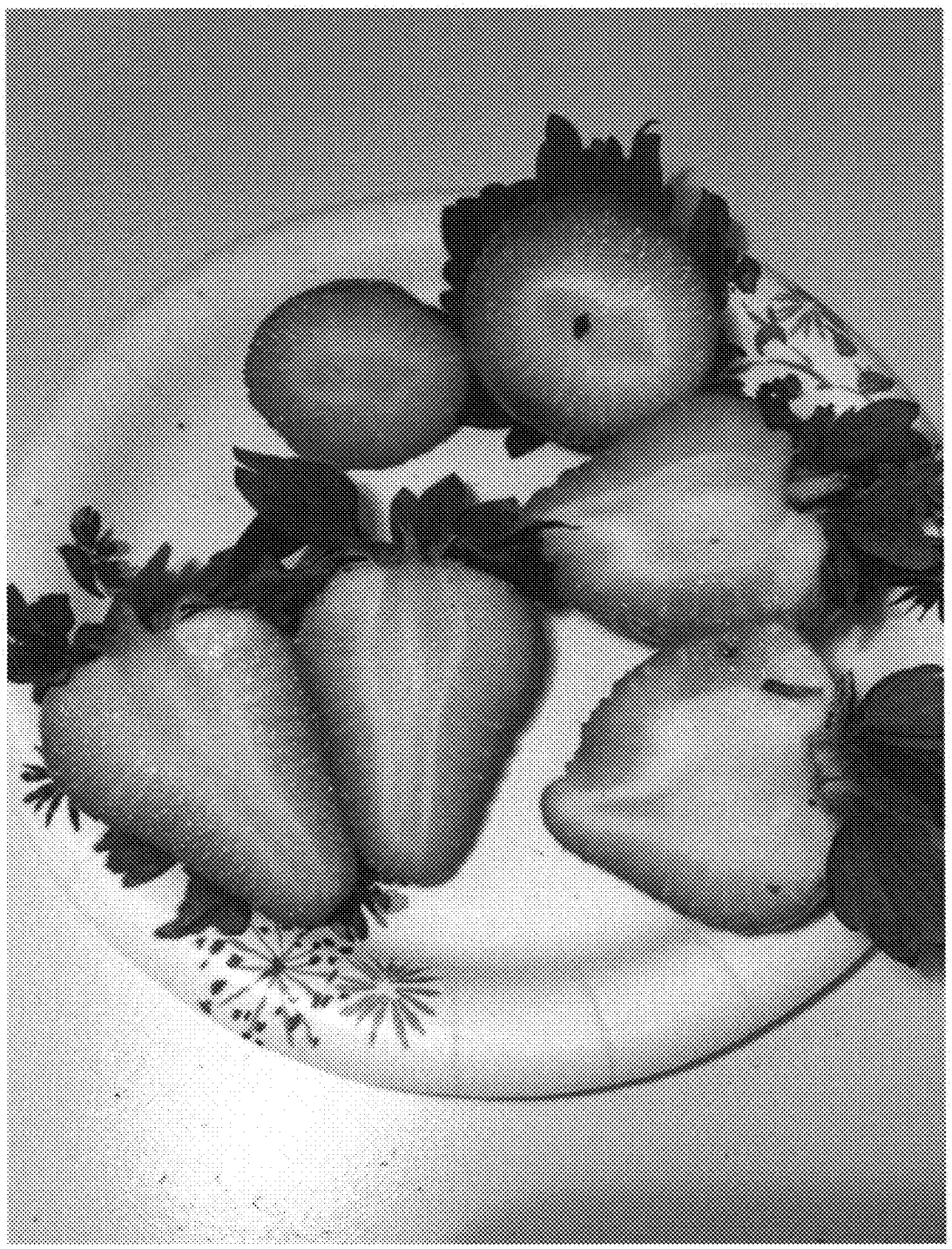
FIG. 3 shows Cross section of early May 'DANI' strawberries.
Figure 4:
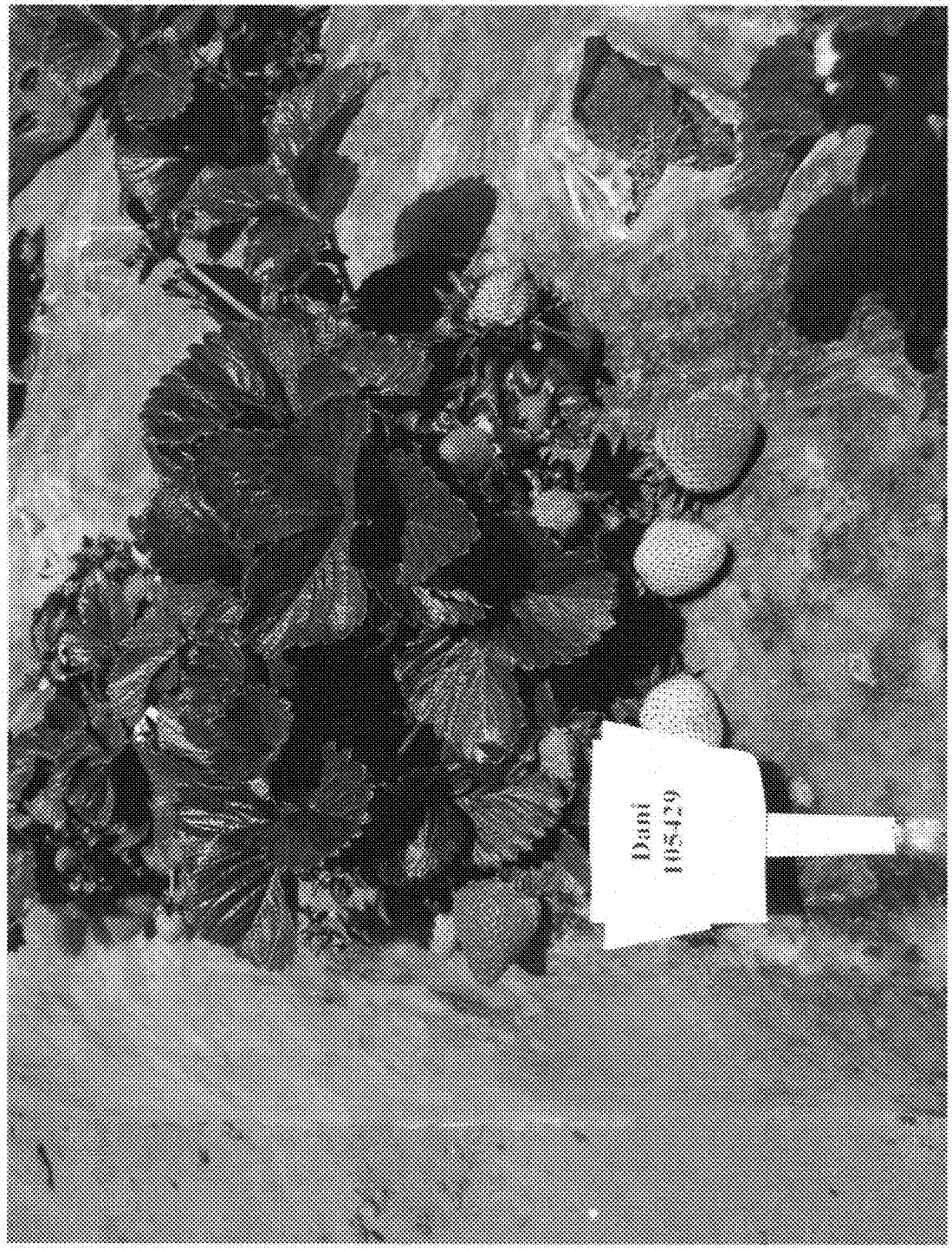
FIG. 4 shows ripe and near-ripe fruits of 'DANI' in May.

'DANI' has not been observed under all possible environmental conditions, and the phenotype may vary significantly with variations in environment. The following observations, measurements, and comparisons describe this plant as grown at California, when grown in the field, unless otherwise noted. As stated above, the color determination is in accordance with The Royal Horticultural Society Colour Chart, 1995 Edition, except where general color terms of ordinary dictionary significance are used. Plants for the botanical measurements in the present application are annual plants.

Botanical classification: 'DANI' is a fertile hybrid derived from a cross.

Common name: Garden strawberry.

General description:

*Plant habit.*—Moderate, coastal climates.

The following description is applied to our plants that are 6 months old as of the time of the measurements.

Classification:

*Species.*—*Fragaria×ananassa.*
*Common name.*—Garden Strawberry.
*Denomination.*—'DANI'.

Parentage:

*Female parent.*—'2002'.
*Male parent.*—'1706'.

Plant:

*Height.*—17.0 cm.
*Diameter.*—25.8 cm.
*Habit.*—Globose, upright.
*Density.*—Medium.
*Vigor.*—Strong.

Terminal leaflet:

*Length.*—6.2 cm.
*Width.*—7.2 cm.
*Length/width ratio.*—0.87.
*Shape in cross-section.*—Concave.
*Blistering.*—Low.
*Glossiness.*—Medium.
*Average number of leaflets.*—Exactly 3.
*Color above.*—Dark Green (RHS 137A).
*Color below.*—Green (RHS 139C).
*Shape.*—Orbicular.
*Margin.*—Crenate to Serrate.
*Venation pattern.*—Reticulate.

Petiole:

*Length.*—9.3 cm.
*Width.*—4.3 mm.
*Color.*—Yellow Green (RHS 145A).

Petiolule:

*Length.*—9.2 mm.
*Width.*—2.7 mm.
*Color.*—Yellow Green (RHS 145A).

Stolon:

*Average daughters/plant.*—About one.
*Diameter.*—3.2 mm.
*Color.*—Dark Purple Red (RHS 53A).

Inflorescence:

*Position relative to foliage.*—At same level.
*Average petals/flower.*—6.
*Petal length.*—14.3.
*Petal width.*—14.3.
*Petal length/width ratio.*—1.0.
*Petal shape/base.*—Orbicular.
*Petal apex.*—Round.
*Petal margin.*—Entire.
*Petal spacing.*—Slightly overlapping.
*Petal color.*—White (RHS 157B).
*Corolla.*—36.7 mm.
*Sepal length.*—23.0 mm.
*Sepal width.*—15.7 mm.
*Sepal length/width ratio.*—1.47.
*Sepal color.*—Dark Green (RHS 137A).
*Calyx.*—60.7 (Diameter relative to corolla: Larger).
*Peduncle.*—12.1 cm.
*Bract frequency.*—Low.

Fruit:

*Fruit truss attitude.*—Prostrate.
*Relative size.*—Large.
*Fruit length.*—39.9 mm.
*Fruit width.*—36.9 mm.
*Fruit length/width ratio.*—1.08.
*Surface color.*—Red (RHS 45A).
*Flesh color.*—Orange Red (RHS 41B).
*Core color.*—White (RHS 155C).
*Shape.*—Predominately conical.
*Average weight/fruit.*—22.0 g.
*Average weight/plant.*—71.8 g.
*Hollow core length.*—10.5 mm.
*Hollow core width.*—6.1 mm.
*Hollow core length/width ratio.*—1.72.
*Insertion of achenes.*—Indented.
*Average achenes/fruit.*—243.
*Firmness of flesh.*—Medium.
*Glossiness.*—Medium.
*Sweetness.*—Medium.

The invention claimed is:

1. A new and distinct cultivar of strawberry plant named 'DANI' substantially as shown and described herein.

* * * * *